United States Patent [19]
Holtmann

[11] Patent Number: 6,031,968
[45] Date of Patent: Feb. 29, 2000

[54] HUMIDIFYING SYSTEM WITH A FILLING LEVEL CONTROL FOR THE LIQUID TO BE EVAPORATED

[75] Inventor: Helmut Holtmann, Stockelsdorf, Germany

[73] Assignee: Drägerwerk AG, Lübeck, Germany

[21] Appl. No.: 08/870,976

[22] Filed: Jun. 6, 1997

[30] Foreign Application Priority Data

Oct. 1, 1996 [DE] Germany ........................ 296 17 077 U

[51] Int. Cl.[7] .............................. F24F 3/14; F16K 31/18
[52] U.S. Cl. ........................... 392/402; 137/430; 73/305
[58] Field of Search .................... 392/386, 387, 392/394, 397, 400, 401, 402, 403, 405, 406; 137/430, 431, 432, 433; 73/305, 308, 309, 322.5

[56] References Cited

U.S. PATENT DOCUMENTS

| | | | |
|---|---|---|---|
| 1,019,603 | 3/1912 | Cornett et al. | 137/433 |
| 1,032,704 | 7/1912 | Risberg | 73/322.5 |
| 1,193,683 | 8/1916 | Glanz, Jr. | 137/131 |
| 1,219,567 | 3/1917 | Leitch | 137/432 |
| 2,302,528 | 11/1942 | Conklin | 392/402 |
| 2,883,511 | 4/1959 | Gooldy | 392/402 |
| 4,905,726 | 3/1990 | Kasugai et al. | 137/433 |
| 5,195,515 | 3/1993 | Levine | 128/203.17 |

FOREIGN PATENT DOCUMENTS 93 07 380  9/1993  Germany .

*Primary Examiner*—Sam Paik
*Attorney, Agent, or Firm*—McGlew and Tuttle, P.C.

[57] ABSTRACT

A humidifying system particularly for incubators and a process for humidifying incubators is disclosed. The system includes a float valve with a sleeve-shaped float housing with a float body axially displaceable therein as well as a throttle valve influencing the flow of liquid. The throttle valve is actuated depending on the relative movement of the float body in relation to the float housing, and by the external diameter of the float body and the internal diameter of the float housing being selected to be such that a capillary gap wetted with liquid is present. With this construction, the reference level for the setting of the liquid level remains unchanged due to the float valve being designed as a hollow float body axially displaceable in a float housing with a liquid-filled, annular capillary gap between the float body and the float housing.

17 Claims, 3 Drawing Sheets

HUMIDIFYING SYSTEM WITH A FILLING LEVEL CONTROL FOR THE LIQUID TO BE EVAPORATED

FIELD OF THE INVENTION

The present invention pertains to a device for setting a liquid level in an evaporating chamber of a humidifying system, and more particularly to a device with a float valve, which detects the liquid level and which influences the flow of liquid in a line extending from a storage tank into the evaporating chamber, such that the predetermined liquid level becomes established in the evaporating chamber.

BACKGROUND OF THE INVENTION

Humidifying systems of this type are preferably used for the artificial respiration of patients. The inhaled air is conditioned to about 34° C. to 37° C. at 80% to 100% relative humidity. Such a humidifying system has become known from DE-GM 93 07 380. In the prior-art breathing air humidifier, the water to be evaporated enters a heated evaporating chamber from a storage tank via a line. The water level in the evaporating chamber is maintained at a constant value by means of a float valve. The float valve, which is a ball valve in this case, is pressed more or less strongly against the outlet opening of the line leading to the storage tank, corresponding to the liquid level present in the evaporating chamber.

The disadvantage of the prior-art breathing air humidifier is that only insufficient control of the liquid level is possible with the ball valve if the evaporating chamber is in an oblique position.

SUMMARY AND OBJECTS OF THE INVENTION

The primary object of the present invention is to improve a device of the above-described type such that accurate setting of the liquid level within the evaporating chamber is guaranteed even in the oblique position of the evaporating chamber.

The object is accomplished by the float valve comprising a sleeve-shaped float housing with a float body axially displaceable therein, wherein a throttle valve influencing the flow of liquid is actuated depending on the relative movement of the float body in relation to the float housing, and by the external diameter of the float body and the internal diameter of the float housing being selected to be such that a capillary gap wetted with liquid is present.

The advantage of the present invention is essentially that the reference level for the setting of the liquid level remains unchanged due to the float valve being designed as a hollow float body axially displaceable in a float housing with a liquid-filled, annular capillary gap between the float body and the float housing, because air bubbles are prevented from escaping from the hollow float body by the capillary gap between the float housing and the float body when the float valve is tilted sideways. In addition, the liquid-filled capillary gap makes possible a low-friction movement of the float body in relation to the float housing, as a result of which the float body responds especially sensitively to slight differences in the liquid level.

The capillary gap between the float body and the float housing is advantageously set such that it is between 0.1 mm and 1 mm. The preferred gap width is 0.2 mm.

The throttle valve preferably comprises a valve body connected to the float body and a valve seat which is located at the float housing and forms the flow outlet of the line.

The valve body and the valve seat advantageously have a conical design. Small liquid volumes can thus be metered particularly well.

The float body may advantageously have a pot-shaped design and be inserted into the float housing pointing with its open end in the direction of a bottom plate of the float housing. The valve body may be fastened at a dome of the float body located opposite the open end.

The valve seat is preferably arranged at a cover closing the float housing.

A connection line may be provided releasing the liquid from the float housing into the evaporating chamber. The connection line is present in the area of the bottom plate.

The device according to the present invention is especially suitable for humidifying the air in an incubator.

One exemplary embodiment of the present invention is shown in the drawing and will be explained in greater detail below.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
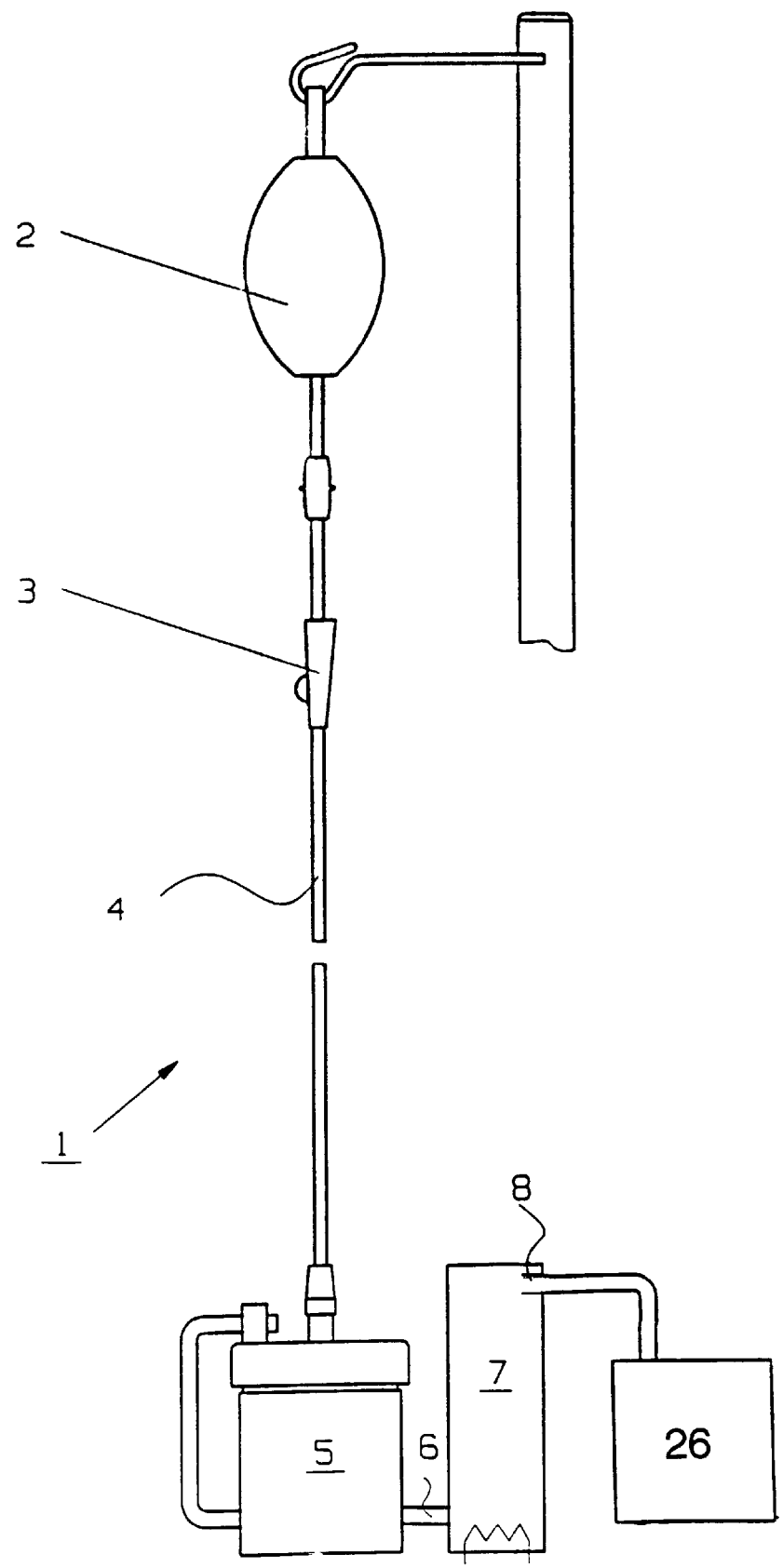
FIG. 1 is a schematic representation of a humidifying system according to the invention.
Figure 2:
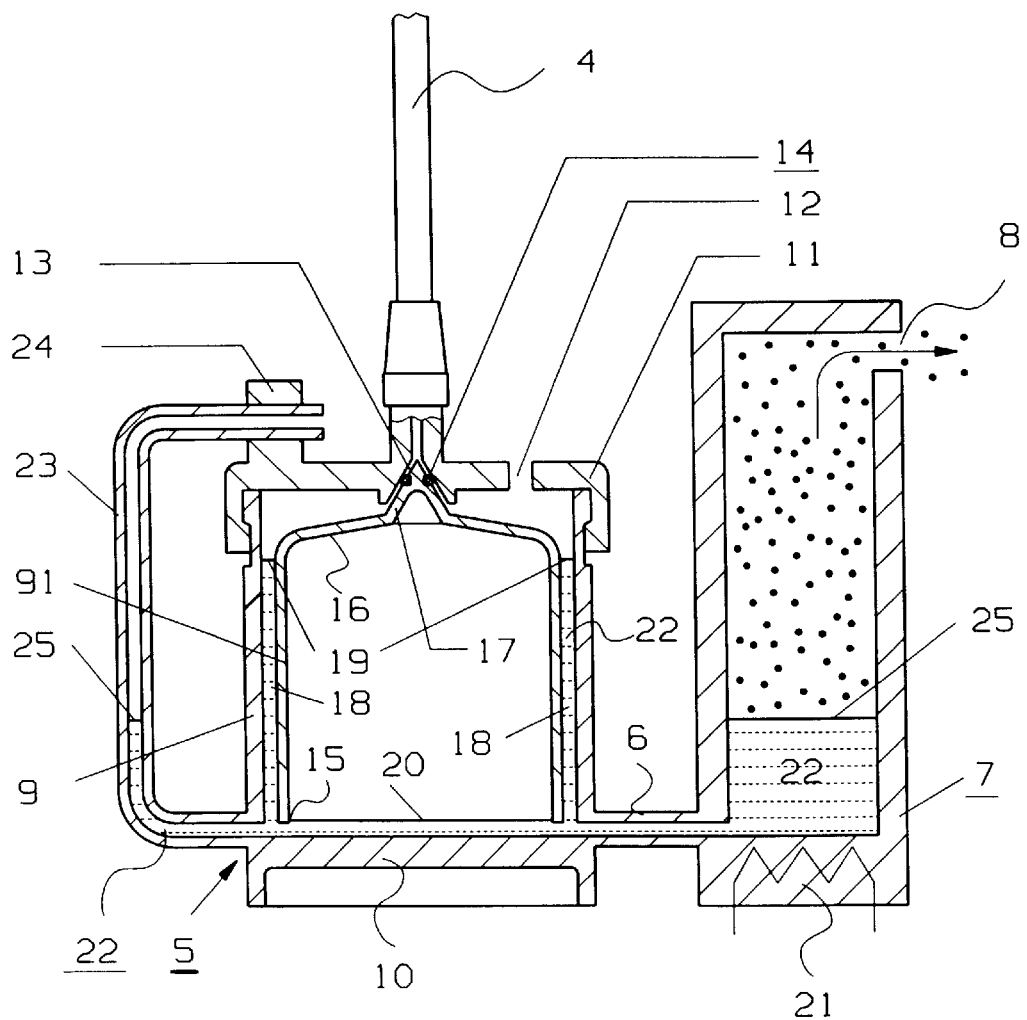
FIG. 2 is the longitudinal sectional view of a float valve and an evaporating chamber in the upright position.

Referring to the drawings in particular, the invention comprises a humidifying system 1 shown in FIG. 1. Liquid is fed in from a loose, flexible bag 2 via a tube clamp 3, a line 4, a float valve 5, and a connection line 6 into a heated evaporating chamber 7. The water vapor being discharged from an evaporating chamber outlet 8 is mixed with the breathing gas of a medical apparatus, e.g., an incubator, 26. The longitudinal section of the float valve 5 and the evaporating chamber 7 are shown in FIG. 2. Identical components are designated with the same reference numbers as in FIG. 1. The float valve 5 comprises a cylindrical float housing 9, which is closed on its underside with a bottom plate 10 and with a cover 11 on the opposite side. A vent hole 12 and a valve seat 13 of a throttle valve 14, with which the flow of liquid within the line 4 is influenced, are located in the cover 11. A cylindrical, hollow, pot-shaped float body 91, whose open end 15 points toward the bottom plate 10 and whose opposite end is directed as a dome 16 toward the cover 11, is accommodated in the float housing 9 in a clearance fit. The cupola roof-shaped area of the dome 16 is designed as a conical valve body, which engages the likewise conical valve seat 13. The valve seat 13 and the valve body 17 form together the throttle valve 14. The liquid 22 present in the line 4 enters the float housing 9 via the throttle valve 14. The external diameter of the float body 91 and the internal diameter of the float housing 9 are selected to be such that a capillary gap 18 having a width of about 0.2 mm is formed, which is filled with liquid 22 and brings about a sealing of the float body 91 against the float housing 9. In addition, the capillary gap 18 makes possible a low-friction axial guiding of the float body 91 within the float housing 9. The liquid levels 19, 20 become established in the float housing 9. The liquid level 20 is approximately at the level of the lower end 15 of the float body 91. Based on the capillary action between the float body 91 and the float housing 9, the liquid level 19 is in the upper range of the capillary gap 18. The connection line 6 branches off in the area of the bottom plate 10 and opens into the evaporating chamber 7. The evaporating chamber 7 has a heating coil 21 in the interior space for evaporating the liquid 22. Besides the connection line 6, a tube 23 is also connected to the float housing 9; this tube 23, bent off in the upward direction, is fastened to a bracket 24 at the cover 11. Since the evaporating chamber 7 is open via the evaporating chamber outlet 8 and the tube 23 is also open on one side, the same liquid level 25 becomes established here according to the principle of communicating tubes. The float body 91 is subject to a lifting force, which corresponds to the weight of the mass of water displaced by the float body 91.

Figure 3:
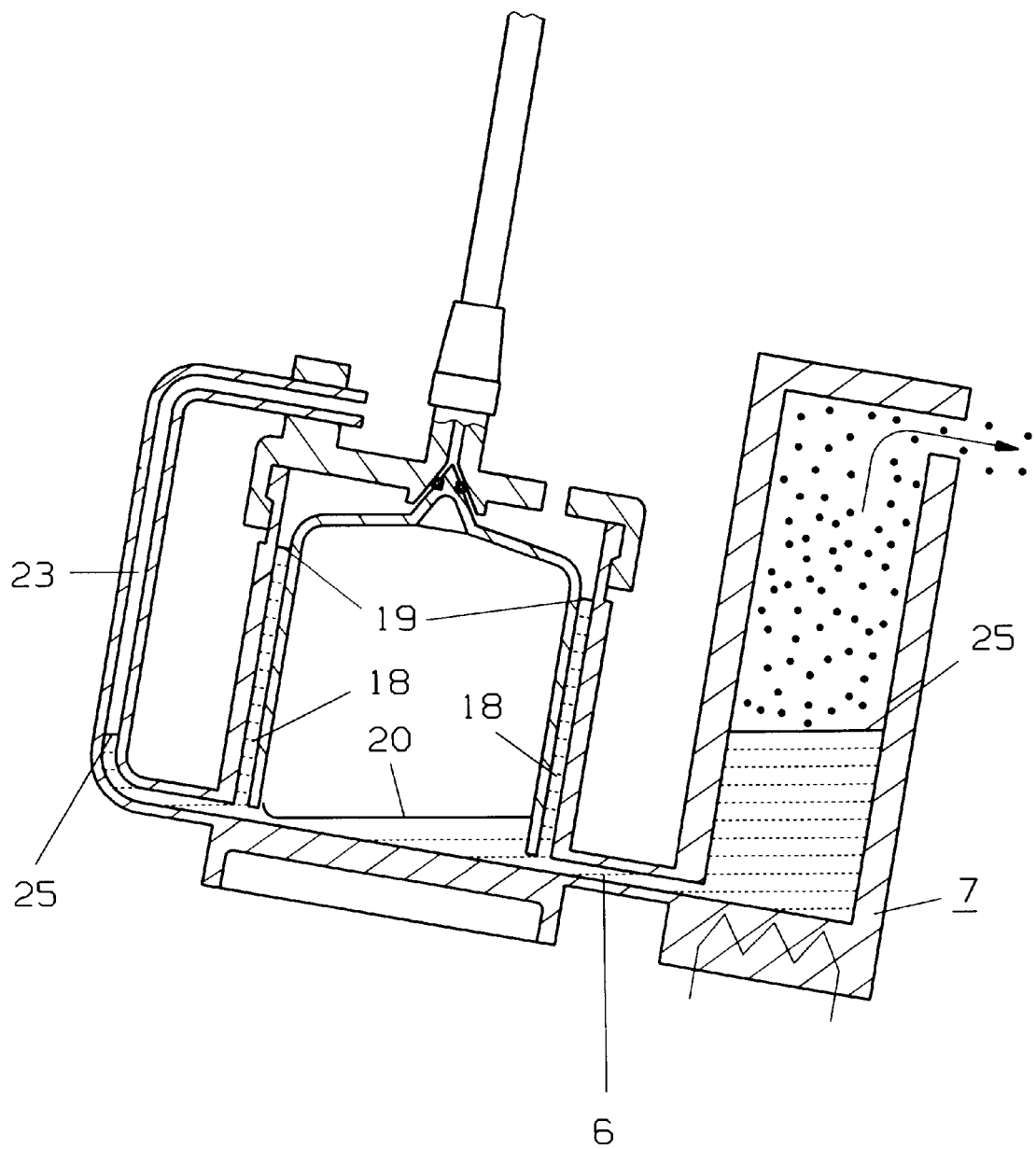
FIG. 3 is an arrangement according to FIG. 2, but in the oblique position.

FIG. 3 shows the float valve 5 and the evaporating chamber 7 in an oblique position. As can be seen from the course of the liquid level line 20, air would now normally escape from the float body 91 through the capillary gap 18 in the upward direction, which would lead to a shift of the liquid level control. Air bubbles are prevented from escaping due to the design of the gap 18 as a capillary gap. Depending on the width of the gap, the float valve 5 can be tilted together with the evaporating chamber 7 by up to 30°. The preferred gap width of the capillary gap 18 is 0.2 mm.

While a specific embodiment of the invention has been shown and described in detail to illustrate the application of the principles of the invention, it will be understood that the invention may be embodied otherwise without departing from such principles.

While a specific embodiment of the invention has been shown and described in detail to illustrate the application of the principles of the invention, it will be understood that the invention may be embodied otherwise without departing from such principles.

What is claimed is:

1. A humidifying system, comprising:
   a storage tank;
   an evaporating chamber;
   a liquid supply line connected to said storage tank and connected to said evaporating chamber;
   float valve means for detecting a liquid level of said evaporating chamber and influencing a flow of liquid in said liquid supply line such that said liquid level becomes established substantially at a predetermined level in said evaporating chamber, said float valve means including a sleeve-shaped float housing, a float body axially displaceable within said float housing and a throttle valve, wherein said throttle valve influencing the flow of liquid is actuated depending on a relative movement of said float body in relation to said float housing, said float body having an eternal diameter and said float housing having an internal diameter selected such that a capillary gap at least partially wetted with liquid is formed between said float housing and said float body, said capillary gap being between 0.1 mm and 1 mm.

2. The system in accordance with claim 1, wherein said capillary gap is 0.2 mm.

3. The system in accordance with claim 1, wherein said throttle valve comprises a valve body connected to said float body and a valve seat located at said float housing, said valve seat forming a flow outlet of said liquid supply line.

4. The system in accordance with claim 3, wherein said valve body and said valve seat have a conical design.

5. The system in accordance with claim 3, wherein said valve seat is arranged at a cover closing said float housing.

6. The system in accordance with claim 1, wherein said float body has a pot-shaped design and is inserted into said float housing pointing with an open end in a direction of a bottom plate of said float housing.

7. The system in accordance with claim 6, wherein said float body includes a dome, and said valve body is fastened at said dome opposite said open end.

8. The system in accordance with claim 6, further comprising a connection line releasing liquid from said float housing into said evaporating chamber, said connection line being provided in an area of said bottom plate.

9. The system in accordance with claim 1, further comprising an incubator connected to said evaporating chamber.

10. The system in accordance with claim 1, wherein:
    said capillary gap forms a seal for blocking passage of gas through said capillary gap.

11. The system in accordance with claim 1, wherein:
    said float body defines an inner chamber with an opening on one end of said float being in communication with an inside of said float housing, said inner chamber forming buoyancy to move said float with said liquid level;
    said capillary gap forms a seal for blocking passage of gas through said capillary gap.

12. The system in accordance with claim 11, wherein:
    said capillary gap blocks passage of gas between said float and said float housing from said one end of said float to another end of said float.

13. The system in accordance with claim 11, wherein:
    said capillary gap is of a size to block passage of gas from said inner chamber to between said float and said float housing when said float valve means is tilted to spill gas from said inner chamber.

14. A process for humidifying the air of an incubator, the process comprising the steps of:
    providing a liquid storage tank;
    providing an evaporating chamber;
    supplying liquid from said storage tank to said evaporating chamber via a liquid supply line;

detecting a liquid level of said evaporating chamber and influencing a flow of liquid in said liquid supply line such that said liquid level becomes established substantially at a predetermined level in said evaporating chamber using a sleeve-shaped float housing, a float body axially displaceable within said float housing and a throttle valve, wherein said throttle valve influencing the flow of liquid is actuated depending on a relative movement of said float body in relation to said float housing, said float body having an external diameter and said float housing having an internal diameter selected such that a capillary gap at least partially wetted with liquid is formed between said float housing and said float body, said capillary gap being between 0.1 mm and 1 mm.

15. The process in accordance with claim 14, wherein said float body has a pot-shaped design and is inserted into said float housing pointing with an open end in a direction of a bottom plate of said float housing.

16. The process in accordance with claim 15, wherein said float body includes a dome, and said valve body is fastened at said dome opposite said open end.

17. The process in accordance with claim 15, further comprising the step of providing a connection line releasing liquid from said float housing into said evaporating chamber, said connection line being provided in an area of said bottom plate.

* * * * *